United States Patent [19]

Schenk

[11] Patent Number: 4,591,726
[45] Date of Patent: May 27, 1986

[54] OPTICAL FAULT SEEKING APPARATUS FOR WEBS

[75] Inventor: Christoph Schenk, Icking, Fed. Rep. of Germany

[73] Assignee: Erwin Sick GmbH Optik-Elektronik, Waldkirch, Fed. Rep. of Germany; 03071986

[21] Appl. No.: 613,829

[22] Filed: May 24, 1984

[30] Foreign Application Priority Data

Sep. 22, 1983 [DE] Fed. Rep. of Germany ....... 3334357

[51] Int. Cl.$^4$ ............................................ G01N 21/88
[52] U.S. Cl. ..................................... 250/572; 356/431
[58] Field of Search ........................ 250/572, 562, 563; 356/430, 431, 444

[56] References Cited

U.S. PATENT DOCUMENTS

| | | | |
|---|---|---|---|
| 4,110,047 | 8/1978 | Takahashi | 250/572 X |
| 4,260,899 | 4/1981 | Baker | 250/563 |
| 4,401,893 | 8/1983 | Dehuysser | 250/572 |
| 4,455,086 | 6/1984 | West | 250/572 X |
| 4,500,208 | 2/1985 | Sick | 356/431 |

FOREIGN PATENT DOCUMENTS 54-45163 10/1979 Japan .................................. 356/431

Primary Examiner—Shrive P. Beck

[57] ABSTRACT

In an optical fault seeking apparatus for webs moved in their longitudinal direction there is provided an optical scanning arrangement which generates a light bead on the surface of the web which moves transversely to the direction of the movement of the web. The scanning arrangement generates several light traces (12, 13, 14) which are displaced in the direction of advance and are parallel to one another. A light receiving arrangement (15) for each light trace has a photoelectric receiver (16, 19; 17, 20; 18, 21). The light traces (12, 13, 14) either adjoin one another or have a distance such that after the passage of the web (22) past all the light traces (12, 13, 14) each web region has been detected once by one scanning light bead (FIG. 1).

4 Claims, 3 Drawing Figures

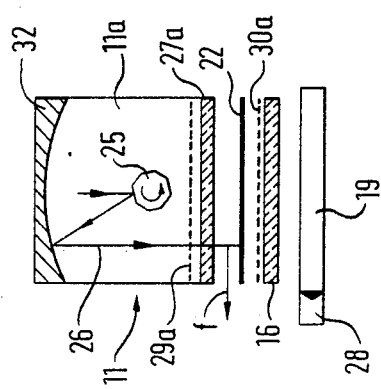
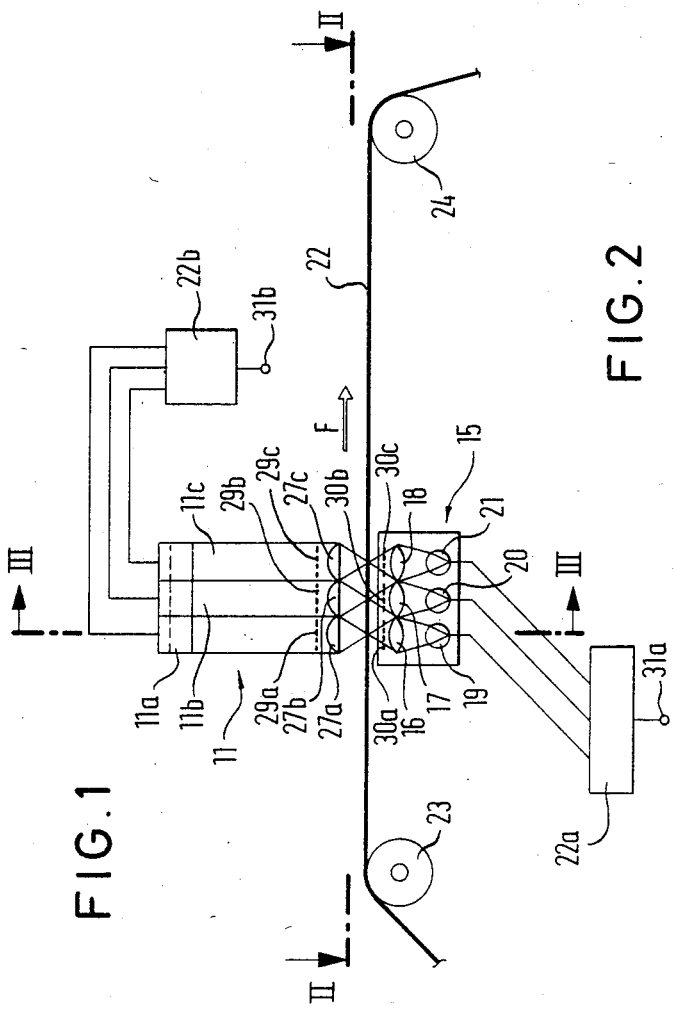

OPTICAL FAULT SEEKING APPARATUS FOR WEBS

The invention relates to an optical fault seeking apparatus for webs which are moved in their longitudinal direction, the apparatus comprising an optical scanning arrangement which generates on the surface of the web at least one light bead which cyclically scans the surface transverse to the direction of movement of the web and thus generates a light trace on the surface of the web which extends transverse to the direction of movement of the web; and a photoelectric light receiving arrangement which receives light reflected from the web and/or light passing through the web in the area of the light bead and transmits a corresponding electrical signal.

Optical fault seeking apparatuses of this kind generally operate with a laser light source the light beam of which is deflected by a mirror wheel or by an oscillating mirror onto a concave mirror whereby a sharply defined scanning beam is obtained which is displaced parallel to itself and which is concentrated by a cylindrical lens onto the material web. The light bead generated in this way cyclically scans the web in its transverse direction so that a narrow light trace or track is created. A light receiving arrangement, for example a light conducting rod having a photoelectric converter arranged at its end face, can be provided in the vicinity of this light trace on one or on both sides of the web. The light receiving arrangement can however also be realised by an autocollimation system in which the light projected onto the web is received again by the optical transmitting system and is then, following the mirror wheel, reflected out to a photoelectric converter, for example by a beam divider. For the inspection of very rapidly moving material webs it is however problematic to obtain a high resolution. For the ideal recognition of small faults of the material web it is namely desirable for the dimensions of the light bead to be selected to be approximately as large as the fault which is to be recognised. In order to ensure gapless scanning of the surface of the material web the material web may not therefore move forwardly in the direction of advance from one scan to the next by more than the extent of the light bead.

The extent of the light bead in the direction of advance is on the other hand preset by the geometry of the faults which are to be recognised. Thus, for rapidly moving webs, if one does not wish to reduce the resolution, there is only the possibility of increasing the scanning speed of the light bead. However, the maximum speed of rotation of the mirror wheel which is generally used is limited for mechanical reasons. Furthermore, on increasing the scanning frequency it is also necessary to process a wider signal bandwidth in the attached electronic processing circuit.

Whereas the limitation of the speed of rotation of the mirror wheel can be overcome by additional electrical and optical measures the bandwidth of the optical-electrical converter and of the subsequent amplifier cannot be straightforwardly increased as desired so that this sets a limit for the scanning frequency which cannot be straightforwardly overcome. Accordingly, when inspecting rapidly moving webs for the smallest point faults the bandwidth limitation presently means that the scanning frequency has to be restricted to a value which lies beneath the mechanical possibilities.

The object underlying the invention is now to provide an optical fault seeking apparatus of the initially named kind by means of which the desired resolution, i.e. the recognition of faults which are of small spatial extent, is possible even with rapidly moving material webs without increasing the scanning frequency.

In order to satisfy this object the invention provides that the scanning arrangement generates a plurality of light traces, preferably two or three light traces, which are displaced in the direction of advance and are parallel to one another; and that the light receiving arrangement has a respective photoelectric receiver for each light trace, with the light traces either adjoining one another or having a spacing such that on passage of the web past all the light traces each point is detected once by one scanning light bead.

Thus, in accordance with the invention, the deficiency which occurs when increasing the speed of movement of the material web without simultaneously increasing the scanning frequency, namely that the web is no longer scanned at all points by the light bead, is overcome by the provision of two or more light scanning beams which are displaced in the direction of advance and which generate light tracks which are parallel to one another. Because a respective photoelectric receiver, to which a customary processing channel is connected, is associated with each scanning light beam, or with each light trace generated on the web, it is possible to obtain a received signal for each location of the web, whereby the overlooking of smaller faults is effectively avoided. In this manner it is possible, by connecting n-channel in parallel to increase the maximum possible speed of advance of the web by a factor n without having to adapt the technology of the signal processing to higher speeds or broader bandwidth. The optical effort required to prepare further scanning light beams can be accurately calculated and remains within reasonable limits because values of two or three are preferably considered for the factor n.

In order to ensure a clear separation of the light originating from the various light traces a preferred further development of the invention provides that the individual light traces are formed by light of different wavelengths and that the photoelectric receivers are matched to the wavelengths of the associated light traces. In this way a problemfree separation of the light from the various light traces is ensured without having to provide different geometrical conditions. One can for example use several light sources with different wavelengths. The received light signals can be separated with the aid of colour filters and associated in this manner with the various processing channels which operate in parallel.

Other advantageous embodiments of the invention are set forth in the subordinate claims 3 to 6.

The invention will now be described in the following with reference to the drawing which shows:

FIG. 1 a schematic sideview of an optical fault seeking apparatus in accordance with the invention arranged at a rapidly moving material web, FIG. 2 a plan view of the material web of FIG. 1 as seen in accordance with the line II—II, and FIG. 3 a section on the line III—III of FIG. 1.

As seen in the drawing a material web 22 is moved at a relatively high speed over deflection rollers 23, 24 in the direction of the arrow F past the optical fault seeking apparatus of the invention, which consists of an optical scanning arrangement 11 and an optical light receiving arrangement 15. As seen in FIG. 1 the optical scanning arrangement comprises three individual light scanners 11a, 11b and 11c which are arranged directly alongside one another and which, in accordance with FIG. 3 generate (by means of a non-illustrated laser light source, non-illustrated optical beam broadening and deflection means, mirror wheels 25 and concave mirrors 32) scanning beams 26 which are displaced parallel to one another and which generate light beads 12a, 13a and 14a on the surface of the material web 22 through cylindrical lenses 27a, 27b, 27c which are arranged directly adjacent the web. On rotation of the mirror wheel 25 in the direction of the arrow of FIG. 3 the scanning beam 26 is displaced parallel to itself in the direction of the arrow f whereby the light beads 12a, 13a and 14a generate respective light traces 12, 13, 14 on the surface of the material web 22. Each light trace 12, 13, 14 extends over the full width of the web 22.

The spatial extent of the light beads or of the light traces in the direction of advance F corresponds to the extent of the smallest fault which is to be recognised.

Cylindrical lenses 16, 17, 18 of the light receiving arrangement 15 are provided beneath the material web in the area of the individual scanners 11a, 11b and 11c. The cylindrical lenses receive the light which passes through any holes in the material web and concentrate it on the input side surfaces of light conducting rods 19, 20, 21. Photoelectric converters are provided at the end faces of the light conducting rods and are connected via electrical lines with an electronic processing circuit 22a (FIG. 1).

Whereas, in the above described hole seeking apparatus, the light receiving arrangement 15 is arranged on the opposite side of the web 22 to the scanning arrangement 11, the scanning arrangement can also operate in autocollimation for the receipt of the reflected light and contain the light receiving arrangement. In this case the received electrical signals are applied to an electronic processing circuit 22b.

Each scanning light bead 12a, 13a and 14a can consist of light of a different wavelength by using light sources of different wavelength or filters 29a, 29b, 29c. The wavelength ranges of the individual light beads should not overlap one another. Corresponding filters 30a, 30b, 30c can then likewise be provided at the light receiving arrangement so that each photoelectric receiver 16, 19; 17, 20 and 18, 21 respectively only receives light from the associated individual scanner 11a, 11b and 11c. In this way an effective decoupling of the neighbouring receiving channels is ensured.

The number of light traces 12, 13 and 14 which are arranged behind one another in accordance with the invention is determined, taking account of the speed of advance of the material web and of the extent of the light beads 12a, 13a and 14a in the direction of movement of the web 22, so that after the web 22 has passed through the optical scanning apparatus of the invention each point of the web has been detected once by one of the light beads 12a, 13a and 14a.

The three input signals can be so combined in the electronic processing circuits 22a and 22b respectively that only a single fault signal which can be used for evaluation or for stopping the material web, appears at the respective output 31a or 31b.

The geometries of the light beads 12a, 13a and 14a are advantageously chosen to be the same.

I claim:

1. An optical fault seeking apparatus for webs moving in their longitudinal direction at a certain speed, the apparatus comprising: an optical scanning arrangement for generating on the surface of the web a plurality of light beads and generating a corresponding plurality of light traces on the surface of the web so that the light traces extend transverse to the direction of movement of the web parallel to each other, with a spacing such that on passage of the web past all the light traces each point is detected only once by a scanning light bead, and a photoelectric light receiving arrangement receiving light reflected from and/or passing throught the web in the area of the light beads, and for transmitting corresponding electrical signals, the light receiving arrangement having a respective photoelectric receiver for each light trace, the light traces being formed by light of different wavelengths, and the photoelectric receivers being matched to the wavelengths of the associated light traces.

2. A fault seeking apparatus in accordance with claim 1, wherein a common light source covering a range of wavelengths is provided for generating each of the individual traces, and wherein the optical scanning arrangement incorporates respective filters for selecting a different wavelength for each trace from said range of wavelengths.

3. A fault seeking apparatus in accordance with claim 1, wherein respective light sources of different wavelengths are provided for each of said light traces.

4. A fault seeking apparatus in accordance with claim 1, wherein respective light sources each covering a range of wavelength are provided for each light trace, and wherein a respective filter is associated with each said light source for selecting a different wavelength for each trace from said range of wavelengths.

* * * * *